US009186409B2

(12) United States Patent
Larsen et al.

(10) Patent No.: US 9,186,409 B2
(45) Date of Patent: *Nov. 17, 2015

(54) SOLID PHARMACEUTICAL COMPOSITION FOR NEUTRALIZING STOMACH ACID

(75) Inventors: Finn Larsen, Bonchester Bridge Hawich (GB); Jens Richard Pedersen, Vejle (DK)

(73) Assignee: S-BIOTEK HOLIDNG APS, Copenhagen K (DK)

(*) Notice: Subject to any disclaimer, the term of this patent is extended or adjusted under 35 U.S.C. 154(b) by 260 days.

This patent is subject to a terminal disclaimer.

(21) Appl. No.: 13/641,163

(22) PCT Filed: Apr. 18, 2011

(86) PCT No.: PCT/DK2011/050125
§ 371 (c)(1),
(2), (4) Date: Dec. 15, 2012

(87) PCT Pub. No.: WO2011/131203
PCT Pub. Date: Oct. 27, 2011

(65) Prior Publication Data
US 2013/0210762 A1  Aug. 15, 2013

Related U.S. Application Data

(60) Provisional application No. 61/351,437, filed on Jun. 4, 2010.

(30) Foreign Application Priority Data

Apr. 23, 2010 (DK) .................................. 2010 70167

(51) Int. Cl.
*A61K 47/02* (2006.01)
*A61K 31/734* (2006.01)
*A61K 9/00* (2006.01)
*A61K 9/20* (2006.01)
*A61K 33/00* (2006.01)
*A61K 33/06* (2006.01)
*A61K 33/08* (2006.01)

(52) U.S. Cl.
CPC .............. *A61K 47/02* (2013.01); *A61K 9/0065* (2013.01); *A61K 9/205* (2013.01); *A61K 9/2009* (2013.01); *A61K 31/734* (2013.01); *A61K 33/00* (2013.01); *A61K 33/06* (2013.01); *A61K 33/08* (2013.01)

(58) Field of Classification Search
CPC ... A61K 9/0065; A61K 9/2009; A61K 9/205; A61K 31/734; A61K 33/00; A61K 33/06; A61K 33/08; A61K 47/02; A61K 2300/00
USPC ........................................................ 514/54
See application file for complete search history.

(56) References Cited

U.S. PATENT DOCUMENTS

| 4,140,760 | A | 2/1979 | Withington |
| 4,172,120 | A | 10/1979 | Todd et al. |
| 6,183,776 | B1 | 2/2001 | Depui et al. |
| 6,348,502 | B1 | 2/2002 | Gardiner et al. |
| 6,395,307 | B1 | 5/2002 | Banning et al. |
| 2002/0045646 | A1 | 4/2002 | Phillips |
| 2003/0176394 | A1 | 9/2003 | Dettmar et al. |
| 2004/0048896 | A1 | 3/2004 | Phillips |
| 2005/0069583 | A1 | 3/2005 | Axford et al. |
| 2005/0202084 | A1 | 9/2005 | Adusumilli et al. |
| 2005/0203035 | A1 | 9/2005 | Tang et al. |
| 2006/0057204 | A1 | 3/2006 | Penhasi et al. |
| 2007/0281015 | A1 | 12/2007 | Los |
| 2011/0287062 | A1 | 11/2011 | Jolliffe et al. |

FOREIGN PATENT DOCUMENTS

| DE | 102006037298 | 2/2008 | |
| EP | 0003589 | 4/1984 | |
| EP | 0 484 106 A1 * | 5/1992 | ............... A61K 9/20 |
| EP | 0484106 | 5/1992 | |
| GB | 1 524 740 * | 9/1978 | ........... A61K 31/715 |
| GB | 1524740 | 9/1978 | |
| GB | 2298365 | 9/1996 | |
| GB | 2324725 | 11/1998 | |
| GB | 2338186 | 12/1999 | |
| WO | 9511668 | 5/1995 | |
| WO | 0187282 | 11/2001 | |
| WO | 03068246 | 8/2003 | |
| WO | WO 03/068246 A2 * | 8/2003 | ........... A61K 31/734 |
| WO | 2005007105 | 1/2005 | |
| WO | 2010015800 | 2/2010 | |

OTHER PUBLICATIONS

Wisniak, J. J. Ind. Chem. Tech., 2003, 10, 99-112.*
Mineral Data Publishing Co. 2005, three separate pages.*
Geology.com, 2005 pp. 1-9.*
International Search Report for PCT/DK2011/050125, Completed by the European Patent Office on Jun. 29, 2012, 6 Pages.
Netzer et al. Aliment Pharmacol Ther 1998, vol. 12, p. 337-342, "Comparison of the effect of the antacid Rennie versus low-dose h2-receptor antagonists (ranitidine, famotidine) on intragastric acidity."
Mandel et al. Aliment Pharmacol Ther 2000, vol. 14, p. 669-690, "Review article: alginate-raft formulations in the treatment of heartburn and acid reflux."

(Continued)

*Primary Examiner* — Ganapathy Krishnan
(74) *Attorney, Agent, or Firm* — Brooks Kushman P.C.

(57) ABSTRACT

A pharmaceutical composition including an alkaline metal alginate, an alkaline salt, and less than 10% by weight based on the weight of the alkaline metal alginate of a calcium salt. The pharmaceutical composition is intended for the treatment or prophylaxis of dyspepsia in a mammal.

4 Claims, 6 Drawing Sheets

(56) References Cited

OTHER PUBLICATIONS

Website http://liveweb.archive.org/http://www.mhra.gov.uk/home/groups/1-unit1/documents/websiteresources/con014065.pdf MHRA 2007, "Public Assessment Report." Retrieved on Feb. 28, 2013, All together 25 Pages.

Website http://web.archive.org/web/20090519074939/http://www.medlineindia.com/alimentarysystem/antacids.htm Medline India, "Medicines Just a Click Away", Dated May 19, 2009, Retrieved on Feb. 28, 2013, 3 Pages.

Website http://www.therapeutiqueinfo/rcp.php?code=18211#A Gavisconell Citron, Comprime A Croquer. Dated Oct. 17, 2008, Retrieved on Feb. 28, 2013, 3 Pages.

Dettmar et al. International Jouranl of Clinical Practice Oct. 2007, vol. 61, No. 10, p. 1654-1662, "The suppression of gastro-oesophageal reflux by alginates."

Feldman., Arch Intern Med Nov. 8, 1993, vol. 153, p. 2415-2424, "Pros and Cons of Over-the-Counter Availability of Histamine2-Receptor Antagonists."

Hampson et al. International Journal of Pharmaceutics 2005, vol. 294, p. 137-147, "Alginate rafts and their characterisation."

Hurlimann et al. The American Journal of Gastroenterol 1996, vol. 91, No. 6, p. 1173-1180, "Effect of Rennie Liquid Versus Maalox Liquid on Intragastric pH in a Double-Blind, Randomized, Placebo-Controlled, Triple Cross-Over Study in Healthy Volunteers."

\* cited by examiner

Dose dependency of tablet according to example 2

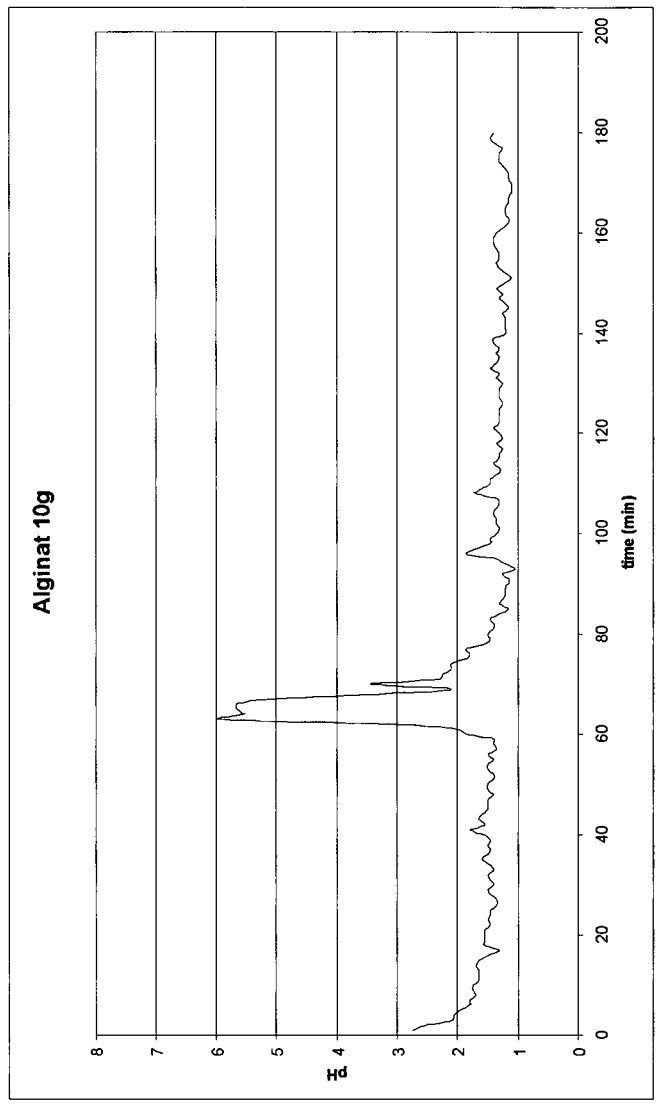

SOLID PHARMACEUTICAL COMPOSITION FOR NEUTRALIZING STOMACH ACID

CROSS-REFERENCE TO RELATED APPLICATION

This application is the U.S. national phase of PCT Appln. No. PCT/DK2011/050125 filed on Apr.18, 2011, which claims priority to Denmark Patent Application No. PA 2010 70167 filed on Apr.23, 2010 and claims the benefit of U.S. Provisional Patent Application No. 61/351,437, filed Jun.4, 2010, the disclosures of which are incorporated in their entirety by reference herein.

The present invention relates to solid pharmaceutical compositions comprising an alkaline metal alginate and an alkaline salt, and uses thereof for treatment or prophylaxis of conditions associated with stomach acid.

BACKGROUND

The stomach may be contemplated to be an extension of the oesophagus, which function is to store the food. The food stays in the stomach between 1 and 6 hours. During the stay the food becomes more like a thin paste or gruel, and is leaked in small portions to the duodenum. In order to process the food several enzymes are produced by the epithelial cells. Furthermore, the parietal cells produce hydrochloric acid, also called stomach acid, which is responsible for the low pH in the stomach. Furthermore, the acid is a first line immune response to foreign organisms by having a sterilizing effect on bacteria, fungi and other microorganisms.

Although a life essential component excess stomach acid is a widespread problem which seems to be related to the lifestyle of today. Stress, wrong intake of food leading to obesity, eating or drinking too quickly, and gulping down frizzy drinks can cause discomfort relating to stomach acid.

Dyspepsia, also known as indigestion, is a general term for the pain or discomfort a person can feel in the stomach and under the ribs, usually after eating or drinking e.g. alcoholic beverages or coffee, although similar symptoms can occur on an empty stomach.

Some people experiences indigestion a few times per year whilst others suffer every day with symptoms ranging from mild discomfort lasting a few minutes to longer lasting severe pain, sometimes accompanied by nausea and vomiting, which can go on for several hours.

The most common indigestion symptoms are: pain or discomfort in the stomach and under the ribs, heartburn, feeling of being bloated or uncomfortably full after eating, rumbling or gurgling noises in the stomach, stomach cramps, a clenched or knotted feeling in the stomach, excessive burping or flatulence, trapped wind, and nausea or vomiting.

The disorder is experienced by an increasing number of people in the developed world. At least one third of the population suffers from episodic dyspepsia. Dyspepsia is generally relieved by antacids. Antacids are normally over-the-counter products, which can be purchased at any pharmacy. Calcium carbonate is commonly used as the active ingredient in antacids. Some calcium-based antacids add other ingredients, such as magnesium or aluminium. Common over-the-counter antacids include: Tums, which is simply calcium carbonate; Rennie, which has magnesium added to ease the potential side effect of constipation with too much calcium; and Maalox, which has aluminium added to calcium carbonate and comes as liquid or tablet forms. Antacids are useful as self-medication in dyspeptic patients with mild or moderate heartburn.

The clinical efficacy of antacids is well documented (Häcki W H: Diskrepanz zwischen In-vivo und In-vitro Säurebindungs-kapazitäten von Magaldrat (Riopan), Gelusil und Maaloxan in Häcki W H, Conti F, Uehlinger M (eds): Magaldrat. Experimentelle und klinische Erfahrungen. Nürnberg, *Verlag Christian M. Silinsky,* 1985, pp 57-61; Hürlimann S, Michel K, Inauen W, Halter F: Effect of Rennie Liquid versus Maalox Liquid on intragastric pH in a double-blind, randomized, placebo-controlled, triple cross-over study in healthy volunteers. *Am J. Gastroenterol.* 1996; 91: 1173-1180; Feldman M: Pros and cons of over-the-counter availability of histamine2-receptor antagonists. *Arch Intern Med* 1993; 153; 2415-2424; Netzer P, Brabetz-Hoefliger A, Bruendler R, Flogerzi B, Huesler J, Halter F: Comparison of the effect of the antacid Rennie versus low dose; and H2-receptor antagonists (ranitidine, famotidine) on intragastric acidity. *Aliment Pharmacol Ther* 1998; 12: 337-342).

Antacids are fast-acting but also short-acting, so they are less useful for frequent or severe heartburn and do not work well as a preventive measure. Acid blockers for heartburn and acid reflux are generally used for severe and chronic symptoms. These drugs work by blocking how much stomach acid is being produced. These acid blockers are not as fast-acting as antacids, but last longer and can be effective for several hours at a time. Over-the-counter acid blockers include Axid, Pepcid, Tagamet, and Zantac. These brands are also available in prescription strength if the more mild forms do not bring enough relief.

Acid blockers work by blocking a type of histamine produced by the stomach, which in turn blocks acid production. These histamine blockers are typically taken twice a day, 30 to 60 minutes before eating to be most effective. The acid blockers are best used as a preventive measure, rather than for sudden, fast relief of symptoms.

Drugs called proton pump inhibitors, or PPIs, shut down tiny proton pumps in the stomach that produce acid, lowering acid levels dramatically. They are often used when histamine blockers do not provide enough relief or when people have erosions in the oesophagus or other complications from GERD (Gastro Esophageal Reflux Disease). One proton pump inhibitor, Prilosec, is available over the counter in certain countries. Others, such as Aciphex, Nexium, Prevacid, Protonix, and stronger Prilosec may require a doctor's prescription depending on the regional requirements.

Reglan is another prescription drug that works to stop acid reflux by speeding up how quickly the stomach empties. Reglan strengthens the digestive contractions that move food through your oesophagus. Faster digestion means less heartburn.

Gaviscon, an over-the-counter heartburn treatment, works as both an antacid and a foam barrier where the oesophagus empties into the top of the stomach. When the tablet is swallowed or the liquid is inBested, the antacid neutralizes stomach acid and the foaming agent creates a physical barrier that helps prevent acid reflux.

Gaviscon is described in GB-A-1,524,740. The prior art document discloses pharmaceutical compositions for the suppression of gastric reflux comprising a low viscosity grade sodium alginate for which the viscosity of a 1% weight volume aqueous solution, when determined on a Brookfield viscometer model RVT using spindle No. 1 at 20 rpm at 25° C. is from 3 to 60 centipoise, from 0.16 to 2.60 parts by weight of sodium bicarbonate per part by weight of sodium alginate and from 0.10 to 1.04 parts by weight of calcium carbonate per part by weight of sodium alginate. The compositions may be administered orally in the form of a dry powder or aqueous suspension which may also contain a suspending agent and/or a preservative. The preparation reacts with gastric acid to form a raft on the contents of the stomach. A liquid formulation comprises an aqueous medium containing 2.5 to 8.0% weight/volume of the low viscosity grade sodium alginate is disclosed. To suspend the calcium carbonate particles in the aqueous medium a suspending agent like acrylic polymer cross-linked with 1% by weight allyl-sucrose is used.

An improved pourability is obtained in GB 2298365 which relates to a pharmaceutical liquid composition comprising potassium bicarbonate instead of sodium bicarbonate and at least 8% w/v sodium alginate. The composition obtains a viscosity which does not possess thickening problems even when stored at low temperatures. The viscosity of a 10% w/v alginate composition falls within the range 200-1500 mPas. The prior art document describes the use of Protanal LFR 5/60 as the alginate of the composition. Salt of divalent metal ions, such as calcium carbonate, are generally included in the pharmaceutical composition in an amount of 8 to 32 g/100 g alginate in order to obtain a satisfying raft formation.

U.S. Pat. No. 6,395,307 also relates to a method for treating reflux oesophagitis as well as dyspepsia using alginates such as Protanal LFR 5/60. It further relates to the preparation of a pourable liquid sodium alginate composition. The composition preferably comprises alginates with a higher mannuronic acid residue to guluronic acid residue ratio and a sodium alginate content of 8 to 15% w/v. The composition further comprises an amount of bicarbonate. The inventors found that bicarbonate, e.g. sodium bicarbonate, is required in order to produce adequate carbon dioxide in the stomach to obtain a proper raft formation of the alginate.

GB-A-2324725 discloses a pharmaceutical composition suitable for forming a mucoadhesive lining in the gastrointestinal tract. It comprises an alginic acid or alginate salt with an M/G ratio of at least unity. The composition may be formulated as a liquid for treatment of reflux oesophagitis. In the examples 32 g calcium carbonate or 100 g of a 10% aluminium hydroxide gel is used per 100 g sodium alginate for the formation of the raft.

WO 01/87282 relates to the treatment of reflux oesophagitis using alginates to inhibit proteolytic enzymes. Especially the invention relates to inhibiting the proteolytic activity of pepsin and/or gastric juice.

According to the invention, one or more sodium alginates with a preferred molecular weight of less than 400 kD are used. The one or more alginate may comprise Protonal LFR 5/60. The pharmaceutical composition may be in the form of a dry powder, which can be admixed with water. Furthermore, the concentration of the preparations in liquid form preferably contains the amount of from 0.1 to 12% w/v of alginate. The viscosity of the solution for LFR 5/60 is measured to 6 mPas for a 1% solution. The composition further comprises a neutralising agent for neutralising gastric acid such as sodium hydroxide.

The composition preferably also comprises divalent or trivalent metal cations to strengthen the formation of a raft. The cations may be calcium or aluminium ions. According to the examples the composition contains in the amount of from 16 to 60 g of calcium carbonate per 100 g alginate.

Gaviscon and similar products exercise its effect by dissolving the solid calcium carbonate salt in the stomach under the influence of the acid gastric fluid. The increasing calcium concentration will stimulate the alginate gelation as calcium ions and the polysaccharides form a rigid matrix. Furthermore, the dissolving of calcium carbonate and sodium bicarbonate will liberate $CO_2$ gas which will be entrapped in the alginate matrix thereby forming foam.

Apart from the inconvenience of the consumption an inhomogeneous product, Gaviscon and products derived thereof furthermore have the disadvantage that the consumer may not obtain the calcium salt in a proper dose for an optimal gelation to progress. More importantly, the sodium alginate salt will not be available and react with the acid present in the stomach because it is occupied with calcium ions in an "egg box" structure.

US 2007/0281015 describes an antacid pharmaceutical composition for the rapid and prolonged neutralization of gastric acidity with mucosa-protecting activity. The pharmaceutical is intended as a liquid preparation for oral ingestion. It includes at least 30% of sodium alginate, an antacid soluble agent, and an inhibitor of proton pump, such as omeprazol. The antacid soluble agent of choice is sodium bicarbonate, which neutralizes hyperacidity acting directly in the digestive tract, the alginate form a viscous suspension or gel after it has entered the stomach environment exerting protecting activity over gastric mucosa, and the inhibitor of a proton pump acts by selectively blocking the $H^+/K^+$-ATPase enzyme of stomach parietal cells.

It is the object of the present invention to bring about anticids containing alginates, which have an instant as well as a longer lasting effect on neutralizing stomach acid.

DISCLOSURE OF THE INVENTION

The present invention presents a solid pharmaceutical composition for neutralizing stomach acid, comprising
an alkaline metal alginate,
an alkaline salt, and
less than 10% by weight based on the weight of the alkaline metal alginate of a salt comprising a cross-linking polyvalent metal ion.

For the purposes of the present invention, dyspepsia includes any medical condition that is caused by gastric acid. In certain aspects of the invention dyspepsia includes gastrooesophageal reflux disease, reflux oesophagitis, gastritis, dyspepsia, peptic ulceration and/or Barretts oesophagus.

Alginate is soluble in water and is activated by acid causing the pharmaceutical composition to become a gel in the stomach due to the low pH value present here. During the gelling process the gastric acid ($H^+$) is consumed, thus resulting in an increase of pH. The rise in pH relieves the symptoms of dyspepsia.

The inventors of the present invention have found that alkali metal alginate possesses a relatively high buffering capacity, which is exerted over a prolonged time period, without the necessity of including an inhibitor of a proton pump, such as omeprazol, lansoprazol, etc. and when alkali metal alginate is combined with an alkaline salt the composition both has a prolonged time period, as well as an instant effect for improved instant relief of dyspepsia. Thus, in a certain embodiment of the invention, the symptoms of dyspeptia caused by excess stomach acid is relieved for 10 minutes or more, such as 15 minutes, more preferably 20 minutes, most preferably 25 minutes or more.

It is presently believed that the effect on dyspepsia is due to the depletion of acid in the stomach subsequently due to reaction with the alginate. The reaction of the gastric acid with alginate results in an increase of the pH value of above a critical value, which alleviates the discomfort of dyspepsia. The gelling of the alginate if ingested in a sufficient amount creates a satiety sensation for the patient resulting in less intake of food. The latter effect is especially importance when the dyspepsic is caused or influenced by obesity or eating habits.

The present invention provides a composition which provides a prolonged time period of neutralisation of stomach acid. In an embodiment of the invention also an efficient disintegration of the composition is devised. Furthermore, by limiting the content of calcium or aluminium ions formation of a raft can be avoided or reduced. Hereby, the carboxylic acid salt groups of the alginate become available for reaction with the stomach acid. The general reaction between the alkali metal carboxylic acid groups of the alkali metal alginate and stomach is illustrated by the reaction scheme below:

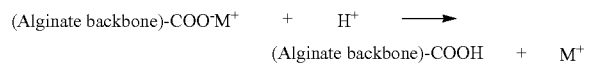

(Alginate backbone)-COO$^-$M$^+$ + H$^+$ ⟶
(Alginate backbone)-COOH + M$^+$

For illustrative purposes only a single carboxylic group is shown on the alginate backbone. The skilled person is aware that a multitude of such groups are present on the backbone. In the present claims and description (Alginate backbone)—COO$^-$M$^+$ is referred to as the alkali metal carboxylic acid group, while such groups when at least partly reacted with acid to form (Alginate backbone)—COOH is referred to as alginic acid.

In one embodiment of the present invention the alkaline metal alginate is sodium alginate. Sodium alginate is widely used by the foods industry to increase viscosity and as an emulsifier. Furthermore, it is a known component in indigestion tablets. A suitable sodium alginate is Protanal LFR 5/60 from FMC Biopolymer AS. This alginate is processed from the plant *Laminaria hyperborean* and has a viscosity in a 1% aqueous solution of 6 mPas, a molecular weight of around 40,000 D, an M/G of around 0.64. Other alginates of interest are SATIALGINE XPU-LVG500, SATIALGINE XPU-LVE500 (DPTJO), and Satialgine S20 from Cargill and Protanal LF10L from FMC Biopolymer AS. Useful alginate having molecular weight between around 150.000 Da and 400.000 Da include Manogel DMB, Manogel GMB, Protonal SF 120 RB, and Protonal GP 5450. Use of another alkaline metal alginate in the present invention may be potassium alginate. Potassium alginate is widely used in foods as a stabilizer, thickener, and emulsifier.

Alginates are polyuronides made up of a sequence of two hexuronic acids: β-D-mannuronic acid and α-L-guluronic acid. Usually, the two sugars are not distributed at random along the chain, but sometimes form blocks of up to twenty units. The proportion of these blocks depends on the species of seaweed and whether the stripe of the blade of the seaweed is used. Less important factors are the degree of maturity, age and where the material was harvested. The ratio of mannuronic to guluronic acid (M/G) in an alginate can vary from 0.4 to 1.6. When the gelling is induced by calcium ions the gelling properties increase with higher content of guluronic acid. The present invention is, however, not particular dependent on the M/G ratio since the gelling of the alginate in the absence of calcium is caused by hydration of the polymer. In a certain aspect an M/G ratio below 1.0 is useful, for example below 0.8, such as below 0.7. The molecular weight of the alginate may be chosen within a range from 10,000 Da to 2,000,000 Da. Generally, a molecular weight below 500,000 Da is desired to ease the dissolution of the solid pharmaceutical composition in the stomach. In a certain embodiment a molecular weight below 200,000 Da is generally desired, such as below 150,000 Da. In another embodiment a molecular weight between 150.000 and 400.00 Da is desired.

In a further embodiment the solid pharmaceutical composition comprises a disintegrating agent.

Bioavailability of a drug depends in absorption of the drug, which is affected by solubility of the drug in gastrointestinal fluid and permeability of the drug across gastrointestinal membrane. The drugs solubility mainly depends on physical-chemical characteristics of the drug. However, the rate of drug dissolution is greatly influenced by disintegration of the tablet.

Disintegrating agents are agents added to tablet formulations to promote the breakup of the tablet into smaller fragments in an aqueous environment thereby increasing the available surface area and promoting a more rapid release of the drug substance. The disintegrating agents can be categorized in three different mechanisms of action; wicking, swelling and deformation.

Effective disintegrating agents that do not swell are believed to impart their disintegrating action through porosity and capillary action, also called wicking. Tablet porosity provides pathways for the penetration of fluid into the tablets. Disintegrating particles with low cohesiveness and compressibility act to enhance porosity and provide these pathways into the tablet. Liquid is drawn up or "wicked" into these pathways through capillary action and rupture the interparticulate bonds causing the tablet to break apart. Materials suitable for acting as wicking agents may be, but are not limited to, colloidal silicon dioxide, kaolin, titanium dioxide, fumed silicon dioxide, alumina, niacinamide, sodium lauryl sulfate, low molecular weight polyvinyl pyrrolidone, m-pyrol, bentonite, magnesium aluminum silicate, polyester, polyethylene, and microcrystalline cellulose.

Swelling is believed to be a mechanism in which certain disintegrating agents such as starch impart their disintegrating effect. By swelling in contact with water or aqueous environment, the adhesiveness of other ingredients in a tablet is overcome causing the tablet to fall apart. Examples of swelling agents may be pregelatinized starch or any type of modified starch, and sodium carboxy methylcellulose.

Deformation is generally thought to be an "elastic" phenomenon where particles deformed under pressure will return to their original shape when the pressure is removed. However, with the compression forces involved with tableting, these particles are believed to be deformed more permanently and are said to be "energy rich" with this energy being released upon exposure to water.

The objectives behind addition of disintegrating agent are to increase surface area of the tablet fragments and to overcome cohesive forces that keep particles together in a tablet.

In a preferred aspect of the invention the disintegrating agent is an alkaline salt. Specific examples include NaHCO$_3$, Na$_2$CO$_3$, KHCO$_3$, K$_2$CO$_3$, and any combinations thereof. The alkaline salt is preferably selected from the group comprising sodium bicarbonate (NaHCO$_3$), potassium bicarbonate (KHCO$_3$), and mixtures thereof. The preferred alkaline salt of the present invention is sodium bicarbonate which provides an optimal disintegration of the pharmaceutical composition. Thereby the disintegrating agent provides a larger surface area of the alkaline alginate and salt to react with the stomach acid which provides a prolonged effect.

In one embodiment the pharmaceutical composition comprises a further alkaline agent selected from the group comprising C$_2$H$_3$O$_2$Na, NaOH, NaH$_2$PO$_4$, Na$_2$HPO$_4$, KH$_2$PO$_4$, KOH, NH$_4$OH, K$_2$HPO$_4$, Mg(OH)$_2$, Zn(OH)$_2$, sodium or potassium silicates, and mixtures of two or more of the further alkaline agents.

The further alkaline salt may be any pharmaceutically acceptable weak base. The group may further comprise sodium or potassium salts of organic acids such as the sodium lactate, disodium malonate, trisodium citrate, and sodium succinate.

The purpose of the further alkaline agent is to provide an instant neutralization of the discomforting symptoms of dyspepsia until the prolonged relief of the alkaline metal alginate.

In a preferred embodiment of the present invention the further alkaline agent is magnesium hydroxide.

It is believed that the further alkaline agent and disintegrating agent provides an instant relief of symptoms of dyspepsia with a time lag. Once these two agents have increased the pH of the stomach the tablet has disintegrated and the alginate will provide the longer lasting effect.

Any base that is considered to be pharmaceutically acceptable may be used in the pharmaceutical composition to provide the instant and short term neutralization.

In a preferred embodiment the amount of sodium bicarbonate is 10% by weight or more, based on the weight of the alkaline metal alginate. In a preferred aspect of the invention, the solid pharmaceutical composition contains an amount of magnesium hydroxide of 2% by weight or more, based on the weight of the alkaline metal alginate.

The amount of sodium bicarbonate may be 100% by weight or less based on the weight of the alkaline metal alginate, such as 80% by weight or less, based on the weight of the alkaline metal alginate, such as 60% by weight or less based on the weight of the alkaline metal alginate, 50% by weight or less based on the weight of the alkaline metal alginate, or 40% by weight or less based on the weight of the alkaline metal alginate. Preferably the amount of sodium bicarbonate may be 10% by weight or more based on the weight of the alkaline metal alginate, such as 15% by weight or more based on the weight of the alkaline metal alginate, such as 20% by weight or more based on the weight of the alkaline metal alginate, such as 25% by weight or more based on the weight of the alkaline metal alginate.

The amount of the further alkaline salt, such as magnesium hydroxide, may be 20% by weight or less based on the weight of the alkaline metal alginate, such as 15% by weight or less based on the weight of the alkaline metal alginate, such as 10% by weight or less based on the weight of the alkaline metal alginate, such as 7% by weight or less based on the weight of the alkaline metal alginate. Preferably the amount of the further alkaline salt may be 1% by weight or more, such as 2% by weight or more, such as 3% by weight or more, based on the amount of the alkaline metal alginate. In a certain embodiment the range of the further alkaline salt is from 1% to 10% by weight based on the weight of the alkaline metal alginate, such as in the range from 2% to 8% by weight based on the weight of the alkaline metal alginate, or in the range from 3% to 6% by weight based on the weight of the alkaline metal alginate.

The pharmaceutical composition of the invention may contain a minor amount of a salt comprising a cross-linking polyvalent metal ion to support the gelation, if desired, when contacted with the gastric juice. The cross-linking polyvalent metal ion may be ions of calcium and aluminium and the salt may as an example be selected among calcium carbonate, $CaHPO_4$, aluminium carbonate and aluminium hydroxide. The salt comprising the cross-linking polyvalent metal ion is usually present in an amount of less than 10% weight, such as less than 5% by weights, such as less than 1% by weights, such as less than 0.3% by weights, preferably less than 0.1% weight, based on the weight of the alginate. The salt is generally solid in the pharmaceutical composition but is suitable highly dissolvable at a pH present in the stomach. In an aspect of the invention the salt provides less than 200 ppm polyvalent metal ions when the pH of the pharmaceutical composition is changed to about pH=2. In a preferred aspect the amount of calcium salt in the pharmaceutical composition provides less than 50 ppm dissolved calcium ions when the pH is changed to about pH=2.

In a preferred aspect, however, the solid pharmaceutical composition of the invention does not contain an added salt comprising a cross-linking polyvalent metal ion, such as a calcium salt, said salt being capable of dissolving at a pH present in the stomach. Insignificant amounts of calcium salts may be present in the tap water used for ingestion of the pharmaceutical composition. In a preferred embodiment at least 70%, such as 80%, preferably at least 90% of the alkali metal carboxylic acid groups of the alkali metal alginate are available for reaction with the stomach acid, i.e. is not reacted with a cross-linking polyvalent metal ion.

The pharmaceutical compositions according to the present invention may comprise one or more pharmaceutical acceptable carriers in addition to the active constituent(s) described above. The carrier(s) must be "acceptable" in the sense of being compatible with the other ingredients of the composition and not deleterious to the recipients thereof. In a certain embodiment, the alginate is purified.

It will be appreciated that the amount of the pharmaceutical composition required for treatment or prevention will vary according to the form of administration, the disorder to be treated, the condition, age, the file history of the subject, and the galenic formulation of the pharmaceutical composition, etc. When treating a patient diagnosed with a certain disease, the amount of active components are preferably effective to alleviate the symptoms of the patient.

The pharmaceutical composition may be formulated as tablets, pills, syrups, capsules, powders, etc.

The term "carrier" refers to a diluent, adjuvant, excipient, or vehicle with which the active components are administered. The carriers in the pharmaceutical composition may comprise a binder, such as microcrystalline cellulose, polyvinylpyrrolidone (polyvidone or povidone), gum tragacanth, gelatine, starch, lactose or lactose monohydrate; a lubricant or surfactant, such as magnesium stearate, or sodium lauryl sulphate; a glidant, such as colloidal silicon dioxide; a sweetening agent, such as sucrose or saccharin; and/or a flavouring agent, such as peppermint, methyl salicylate, or orange flavouring.

Therapeutic formulations suitable for oral administration, e.g. tablets and pills, may be obtained by compression or moulding, optionally with one or more accessory ingredients. Compressed tablets may be prepared by mixing the constituent(s), and compressing this mixture in a suitable apparatus into tablets having a suitable size. Prior to the mixing, the alkaline metal alginate may be mixed with a binder, a lubricant, an inert diluent and/or a disintegrating agent and the alkaline salt may be mixed with a diluent, a lubricant and/or a surfactant.

When one or more carriers are present, free-flowing alkaline metal alginate powder is mixed with a binder, such as microcrystalline cellulose, and a surfactant, such as sodium lauryl sulphate, until a homogeneous mixture is obtained. Subsequently, another binder, such as polyvidone, is transferred to the mixture under stirring. When a uniform distribution is obtained the alkaline salt is added under constant stirring. This mixture is passed through granulating sieves and dried by desiccation before compression into tablets in a standard compressing apparatus. Alternatively, the tablets are prepared without the addition of carriers. According to this alternative embodiment the free-flowing alkaline metal alginate is mixed with an alkaline salt before the mixture is compressed into tablets. Conventional methods for producing a solid form of the pharmaceutical composition may be found in the European Pharmacopoeia, which is included herein by reference.

A tablet may be coated or uncoated. An uncoated tablet may be scored. A coated tablet may be coated with sugar, shellac, film or other enteric coating agents.

In order to illustrate the invention the following examples are included. These examples do not limit the invention. They are meant only to suggest a method of practicing the invention. Those knowledgeable in manufacturing tablets may find other methods of practicing the invention. However, those methods are deemed to be within the scope of this invention.

FIGURES

FIG. 6 illustrates the median pH of the test group receiving 10 g alginate according to example 4.

EXAMPLES

Example 1

Preparation of Tablets

Tablets were prepared by dry mixing 1250 g Protanal LFR 5/60 sodium alginate obtained from FMC BioPolymer and 375 g of sodium bicarbonate. The mixture was compressed to tablets having a weight of 1250 mg.

Example 2

Preparation of Tablets with Mg(OH)$_2$

Tablets were prepared by dry mixing 1250 g Protanal LFR 5/60 sodium alginate obtained from FMC BioPolymer, 375 g of sodium bicarbonate and 50 g magnesium hydroxide. The mixture was compressed to tablets having a weight of 1250 mg.

Example 3

Dose Response Experiment

The aim of the study is to compare the dose response from the tablets according to Example 1 with the dose response from the tablets according to Example 2 with respect to its acid inhibitory potency with a special interest in the time lag before acidity reaches a pH<2.5.

Method and Material

An aqueous composition of 10% (w/v) of tablets prepared as described in Example 1 was compared with an aqueous composition of 10% (w/v) of tablets prepared as described in Example 2 in a titration assay.

The stock alginate solutions were prepared by dissolving 1, 2, 4, 6, and 8 tablets according to Example 1, respectively, in 100 ml Milli-Q H$_2$O for about 1 hr in a beaker with magnet stirring at full speed. Analogous solutions of tablets according to Example 2 were prepared. The final Protanal amount is shown in Table 1 below. Then dissolved 0.267 g sodium bicarbonate and 0.160 g calcium carbonate was added to each solution. 10 ml of the stock solution was used in the titration assay. The titration assay was performed at 20-28° C.

TABLE 1

| No. of tablets dissolved | Protanal amount (g) |
|---|---|
| 1 | 0.125 |
| 2 | 0.250 |
| 4 | 0.500 |
| 6 | 0.750 |
| 8 | 1.000 |

The example 1 solution and the example 2 solution were titrated using 0.1M HCl. Every 30 sec the volume used for titration, mmol H$^+$ and pH for each example 1 solution and example 2 solution were recorded until a pH of approximately 2.5 was reached.

Figure 1:
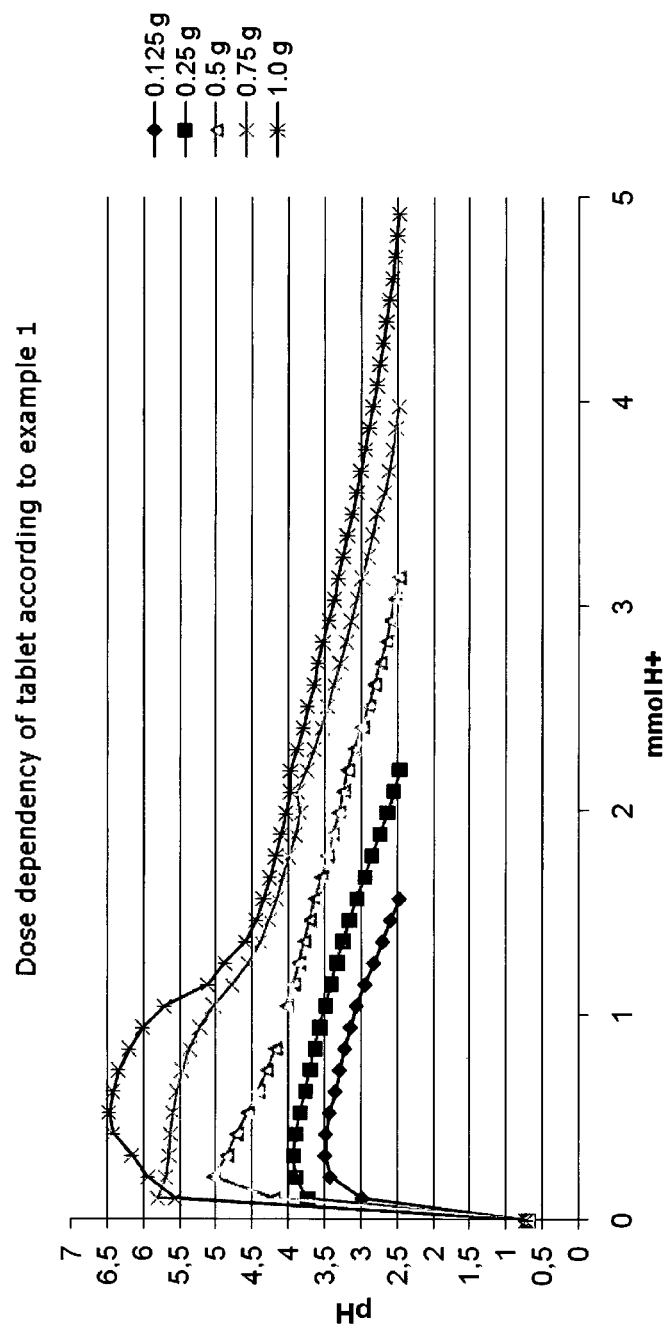
FIG. 1 illustrates the results of the dose dependency of a composition according to example 1 in a titration assay.
Figure 2:
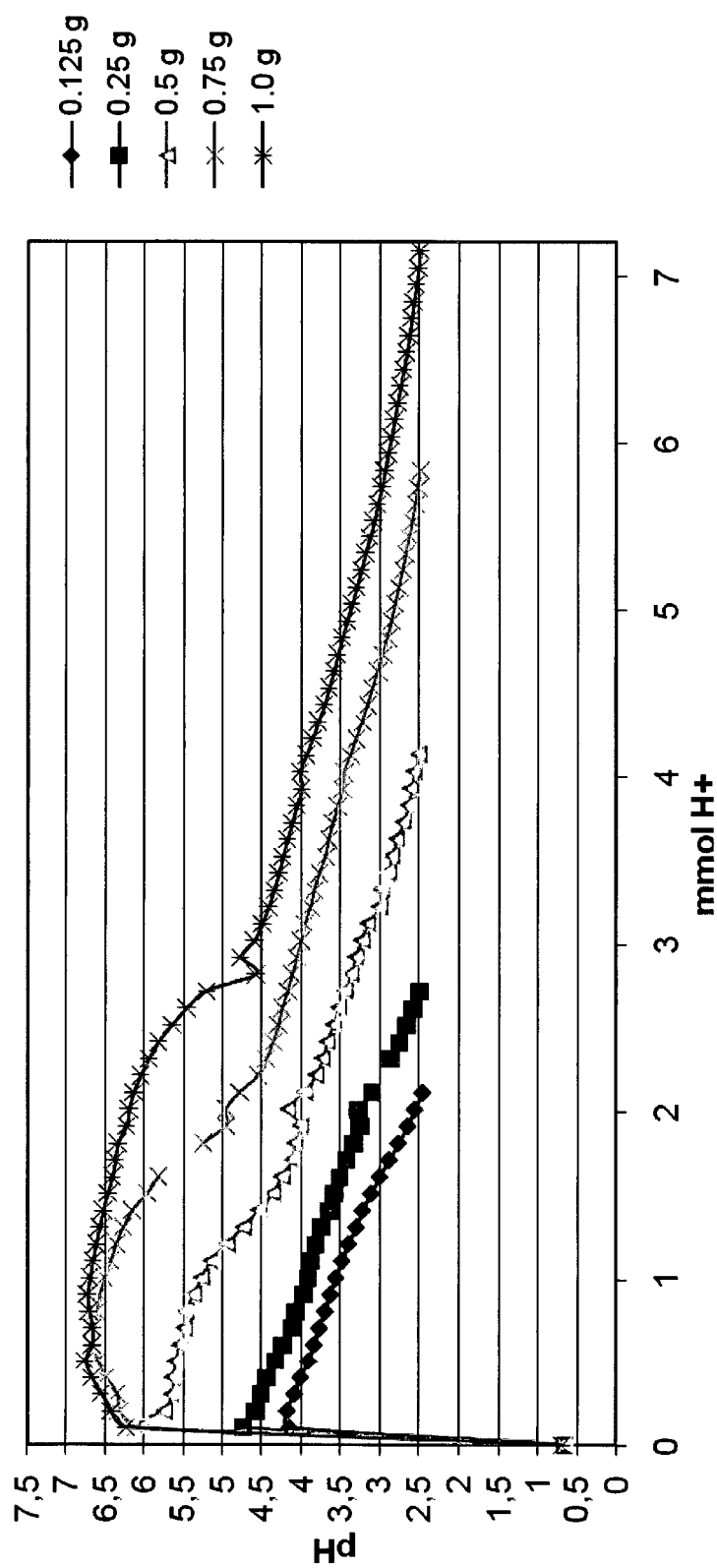
FIG. 2 illustrates the results of the dose dependency of a preferred embodiment according to claim 2 in a titration assay.

The results obtained in the study are shown in FIG. 1 for the titration of the example 1 solution and in FIG. 2 for the titration of the example 2 solution.

Results

The pH was comparable between the example 1 solution and the example 2 solution before titration was started (approximately 0.7). Therefore, measurements can be compared between the solutions. At the first measurement after 30 sec pH was increased. However, the pH for the example 2 solution had a higher increase than for the example 1 solution.

The illustration on FIG. 2 clearly shows an instant and prolonged increase of pH when titrating the sample solution compared to the illustration on FIG. 1. A comparison of the area below the curves shows that for all the Protanal LFR 5/60 concentrations of the example 2 solutions titrated the area is larger than for the example 1 solutions.

Conclusion

In this study it has been demonstrated that the present pharmaceutical composition comprising sodium alginate Protanal LR 5/60, and sodium bicarbonate has an instant and prolonged effect on pH value in a titration assay. The effect is increased when magnesium hydroxide is added.

Example 4

Cross-Over Study

The aim of the study is to compare three different doses of the tablets according to example 2 with respect to its gastric acid inhibitory potency with a special interest in the time lag before intragastric acidity reaches a pH>3.0. This acidity value threshold is considered for the efficacy of gastric anti-secretory drugs.

Material and Methods

The study was conducted as a single blind, randomized, placebo-controlled, four way cross-over study. The aim is to compare the activities of the antacid test Compound, S-B Protanal 5/60 combined with an alkaline agent, to placebo with respect to various intragastric acidity parameters. The study was conducted in accordance with the ethical principles of the Declaration of Helsinki and the international principles of Good Clinical Practice.

S-B Protanal 5/60 is an alginate with jellyfing properties when exposed to acid (gastric acidity is in the order of 1.5-2.0). It is speculated that the test drug will immediately bind HCl and subsequently have an immediate and long-lasting effect in terms of raising pH to 3 or more.

Subjects

Twelve healthy male, *H. pylori*-negative, subjects participated in this study. They all had clinically normal physical findings, no history of hepatic or significant gastrointestinal disease and did not take regular medication. A full medical history has taken and a physical examination was performed.

Subjects had given written informed consent before entering the study. The study was submitted and approved by the local ethical committee of Basel.

Exclusion criteria was:
digestive surgery (with the exception of appendectomy)
any clinically relevant ECG abnormality
history of clinically significant hepatic/renal/respiratory/neurological/endocrine/hematological disorders
any regular medication including over-the-counter drugs
any investigational drug/treatment and/or taking part in any other clinical study within the previous 2 months
alcohol consumption of >5 units daily and/or >20 units weekly
history of drug, alcohol or other substance abuse or other factors limiting the ability to co-operate Study Procedures Each subject underwent four different treatments after an overnight fast of at least 10 hrs. On four different days and in random order, each study participant received three different doses (1.25 g; 5.0 g and 10.0 g) of test alginate compound, S-B Protanal 5/60, and placebo (control treatment). The test drug was swallowed and followed by an oral intake of 100 ml of tap water. On each study day the subject received test tablets followed by 100 ml of water or for placebo 100 ml of water, only.

Tablet Allocation:
1.25 gram active: 1 active test tablets+100 ml of tap water
5.0 gram active: 4 active tablets+100 ml of tap water
10.0 gram active: 8 active tablets+100 ml of tap water
Placebo: 100 ml of tap water The treatments were separated by a wash-out phase of at least four days.

For the intragastric pH monitoring a glass electrode (Medical Instruments Corporation, Solothurn, Switzerland) was used which was attached to a Digitrapper Mark III GastrograpH (Medical Instruments Corporation). The electrode was calibrated in buffer solutions at pH 7.0 and 1.7 before and after each recording. The pH electrode was inserted transnasally into the gastric body by a skilled person at the study site. The position of the pH electrode in the stomach was 8-10 cm below the gastro-oesophageal junction, which was recognized by an abrupt drop in pH from neutral (oesophageal pH 5-7) to acid (intragastric pH<2). Sudden changes in recorded pH can be caused by differences in intensity of contact between electrode tip and the gastric mucosa. Variations in the intensity of contact can also be caused by gastric motility and changes in body position. In order to reduce the incidence of these artifacts, all subjects were asked to remain in an upright position.

Measurements of the intragastric pH continued for a basal period of 60 min. During this period, the intragastric pH had to be <3.0 for at least 50% of the recording time. If this was not the case, the entire pH measurement was repeated. After the basal period, one of three doses of test drug or placebo was administered according to the randomization scheme and the pH monitoring continued for the following 2 hrs.

Study Parameters

The primary endpoint of the study was the lag time before an intragastric pH>3.0 was reached for a minimum of 10 consecutive minutes after drug administration. Secondary endpoints included (1) peak pH, (2) percentage of time with pH>3.0, (3) the lag time before the peak pH reached after the initial 10-min period at pH>3.0, (4) median pH during the first 60 min after drug administration and (5) integration of time period with pH>3.0 after drug administration. The safety was evaluated by assessment of adverse events.

Statistical Analysis

The pH values are shown as median curve; the time intervals as box whisker plot with 25 and 75% intervals. Comparisons of the different treatments was done by non-parametric Wilcoxon signed ranks test with Bonferroni's correction, also a comparison between the three alginate doses was performed, although the study was not powered to detect a different between the three different doses of active treatment. All statistical tests was two-tailed and p<0.05 was accepted as statistically significant. The same procedure was used for the secondary objectives.

Results

Figure 3:
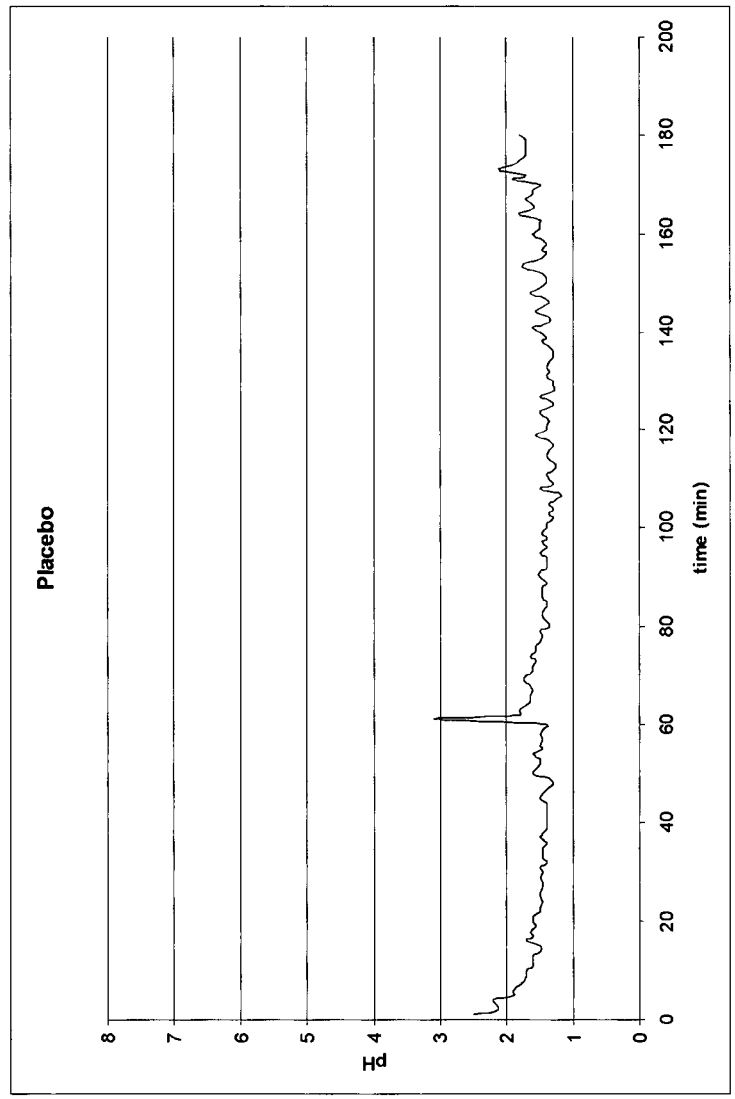
FIG. 3 illustrates the median pH of the placebo results according to example 4.
Figure 4:
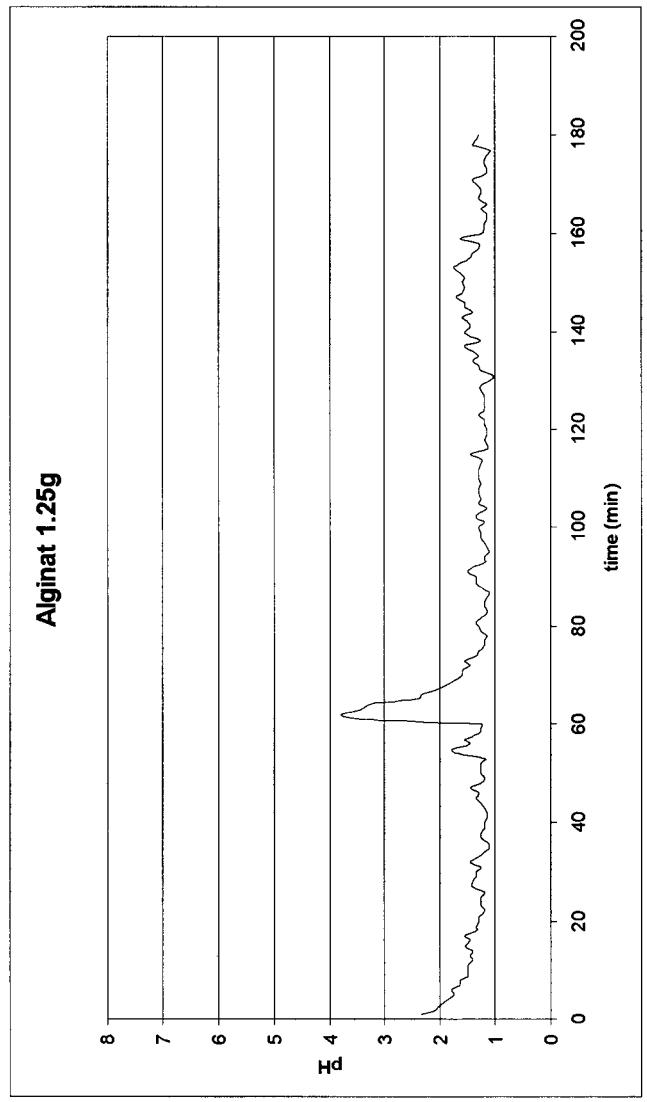
FIG. 4 illustrates the median pH of the test group receiving 1.25 g alginate according to example 4.
Figure 5:
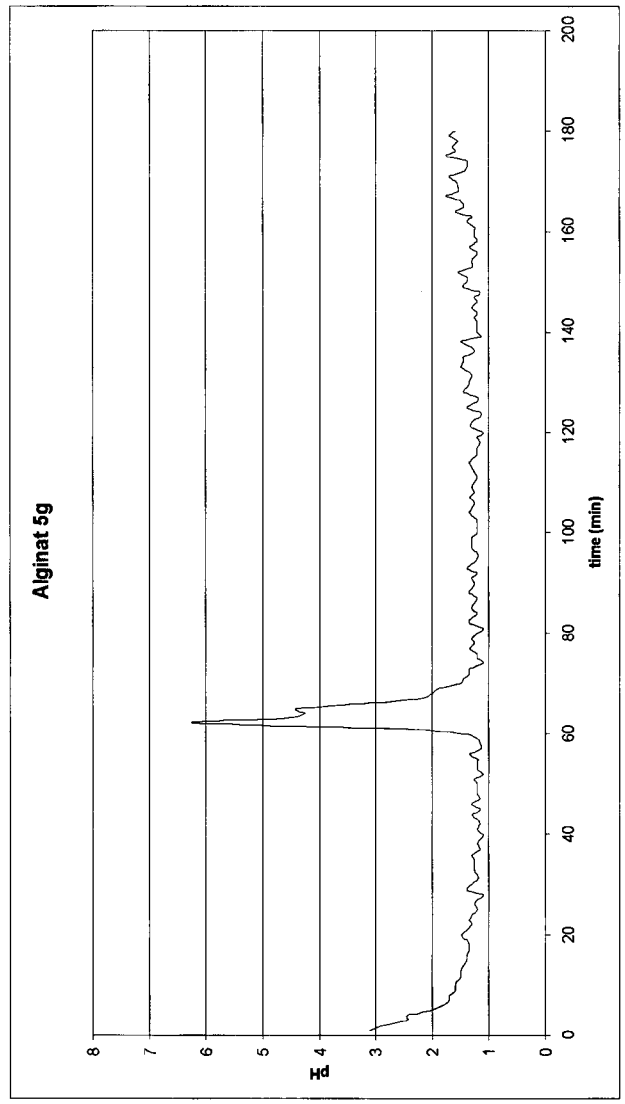
FIG. 5 illustrates the median pH of the test group receiving 5 g alginate according to example 4.

The results obtained are illustrated in FIGS. 3 to 6, wherein FIG. 3 illustrates the results from the group of test subjects receiving placebo and FIGS. 4 to 6 illustrate the results from the group of test subjects receiving test compounds according to the present invention in three different amounts.

In comparison to placebo all three tested doses of test compound increased pH.

The onset of action in terms of increase in pH happened within minutes and a prolonged effect was observed for all three groups receiving test compounds.

On FIGS. 4 to 6 an increase of pH is seen at 60 minutes where the test compound is administered. The increases have three independent peaks which presumably illustrate the neutralizing effect of magnesium hydroxide, sodium bicarbonate, and alginate, respectively. The effect is obtained for as long as approximately 20 minutes before the pH reaches baseline.

The invention claimed is:

1. A solid pharmaceutical composition for neutralizing stomach acid, comprising
   sodium alginate,
   an alkaline salt, wherein the alkaline salt is a disintegrating agent selected from the group consisting of sodium bicarbonate ($NaHCO_3$), potassium bicarbonate ($KHCO_3$), and mixtures thereof,
   2% by weight or more, based on the weight of the sodium alginate, of a further alkaline agent selected among the group consisting of magnesium hydroxide ($Mg(OH)_2$), potassium hydroxide (KOH), sodium hydroxide (NaOH), sodium acetate ($C_2H_3O_2Na$), and mixtures thereof, and
   less than 10% by weight based on the weight of the sodium alginate of a salt comprising calcium.

2. The solid pharmaceutical composition according to claim 1, wherein the further alkaline agent is magnesium hydroxide.

3. The solid pharmaceutical composition according to claim 1, wherein the amount of sodium bicarbonate is 10% by weight or more, based on the weight of the sodium alginate.

4. The solid pharmaceutical composition according to claim 1, wherein the amount of magnesium hydroxide is 4% by weight or more, based on the weight of the sodium alginate.

* * * * *